United States Patent

Mikasa et al.

[11] Patent Number: 4,727,746
[45] Date of Patent: Mar. 1, 1988

[54] METHOD OF MODAL MASS ANALYSIS OF EXHAUST GAS FROM A MOTOR VEHICLE

[75] Inventors: Hajime Mikasa; Hideji Kitamura, both of Kyoto, Japan

[73] Assignee: Horiba, Ltd., Kyoto, Japan

[21] Appl. No.: 948,037

[22] Filed: Dec. 31, 1986

[30] Foreign Application Priority Data

Dec. 31, 1985 [JP] Japan .................. 60-298457

[51] Int. Cl.⁴ .................................. G01N 1/00
[52] U.S. Cl. ................................ 73/23; 73/116
[58] Field of Search .............. 73/23, 116, 117.3

[56] References Cited

U.S. PATENT DOCUMENTS

| | | | |
|---|---|---|---|
| 3,406,562 | 10/1968 | Perna, Jr. et al. | 73/23 |
| 3,593,023 | 7/1971 | Dodson et al. | 73/23 |
| 3,603,155 | 9/1971 | Morris et al. | 73/23 |
| 4,160,373 | 7/1979 | Fastaia et al. | 73/23 |
| 4,586,367 | 5/1986 | Lewis | 73/23 |

*Primary Examiner*—Stewart J. Levy
*Assistant Examiner*—Hezron E. Williams
*Attorney, Agent, or Firm*—Wenderoth, Lind & Ponack

[57] ABSTRACT

A method of measuring the quantity of an ingredient gas in the exhaust gas from a motor vehicle during each of a sequence of driving modes by measuring and storing in real time flow rate data $Q_E(t)$ representative of the flow rate of the exhaust gas at a succession of times during a driving mode, measuring and storing concentration data representative of the concentration of the ingredient gas in the exhaust gas during a time period delayed with respect to the time period of the driving mode in order to compensate for a time delay in correspondence between changes in flow rate and performing an interpolation method and either a data-compression or data-expansion method on the concentration data in order to obtain corrected concentration values $C_E(t)$ on a one-to-one basis in phase and magnitude to the flow rate data, and determining the quantity $M(t)$ of the ingredient gas in the exhaust gas for each of the measurements of flow rate based on the operational equation $M(t)=\rho \times C_E(t) \times Q_e(t)$, wherein $\rho$ is the density of the ingredient gas.

2 Claims, 5 Drawing Figures

METHOD OF MODAL MASS ANALYSIS OF EXHAUST GAS FROM A MOTOR VEHICLE

BACKGROUND OF THE INVENTION

1. Field of the Invention

The present invention relates to a method of conducting a modal mass analysis for measuring a quantity of each specified ingredient gas among ingredient gases to be measured such as CO, $CO_2$, $NO_x$, HC and the like, in an exhaust gas from a motor vehicle for various modes of driving (idling, accelerating, constant-speed driving and decelerating), and in particular, to a method of conducting a modal mass analysis of an exhaust gas from a motor vehicle on the basis of a procedure that a flow rate $Q_E(t)$ of the exhaust gas exhausted from a motor vehicle tested in a driving simulation having an appointed driving-mode change-over sequence, is measured in an appointed sampling time period and a concentration $C_E(t)$ of an ingredient gas to be measured in the exhaust gas is measured in the same sampling time period as in the measurement of said flow rate $Q_E(t)$ of the exhaust gas, and then a quantity $M(t)$ of the ingredient gas in the exhaust gas is determined for each driving mode by the use of the following equation (2):

$$M(t) = \rho \times C_E(t) \times Q_E(t) \quad (2)$$

wherein $\rho$ is a density of the ingredient gas to be measured.

2. Prior Art

Many prior methods are well known for such a method of conducting a modal mass analysis of an exhaust gas from a motor vehicle. In one such method, a dilute stream method, a flow rate (constant for each system) of a diluted exhaust gas is used as the flow rate $Q_E(t)$ in equation (2) and a measured result of a concentration of an ingredient gas in the diluted exhaust gas is used as the concentration $C_E(t)$ in equation (2).

In a second prior method, a $CO_2$-tracing method, the flow rate $Q_E(t)$ in equation (2) is determined by comparing the result of a measurement of the concentration of $CO_2$ in a raw (undiluted) exhaust gas with the measured concentration of $CO_2$ in the exhaust gas after the exhaust gas has been diluted, and the result of a measurement of concentration of an ingredient gas in the raw exhaust gas is used as the concentration $C_E(t)$ in equation (2).

In a third method, a dilution air quantity method, the flow rate $Q_E(t)$ in said equation (2) is determined as a difference between a flow rate (constant for each system) of the diluted exhaust gas and a measured dilution air quantity, and a measured concentration of the ingredient gas in the raw exhaust gas is used as the concentration $C_E(t)$ in equation (2).

However, in every case both the measurement of the flow rate $Q_E(t)$ of the exhaust gas and the measurement of the concentration for determining the concentration $C_E(t)$ of the ingredient have been carried out without a substantial delay relative to a point in time of change in driving mode and in an appointed common sampling time.

However, the above described conventional methods have shown the following vital disadvantages:

Referring to FIG. 4, there is shown a timing chart schematically showing representative changes in exhaust gas flow ($Q_E$) and exhaust gas ingredient concentrations ($C_E$) from a motor vehicle on a real time basis for different driving modes, in which IDL indicates an idling driving mode, ACC indicates an accelerating driving mode, CRU indicates a constant-speed driving mode and DEC indicates a decelerating driving mode, the driving modes being changed over on the basis of an appointed sequence. As is apparent from this chart, the flow rate $Q_E(t)$ of the exhaust gas is changed following each driving mode changes at times $H_1$, $H_2$, $H_3$, $H_4$ nearly without any delay, while the concentration $C_E(t)$ of the ingredient gas is changed respectively following certain delay times $\tau_1$, $\tau_2$, $\tau_3$, $\tau_4$ relative to the respective change-over times $H_1$, $H_2$, $H_3$, $H_4$, due to a delay in response incidental to a piping system and a gas-concentration analyzer, absorption and desorption phenomena of ingredient gases to be measured and the like. In addition, since each of said delay times $\tau_1$, $\tau_2$, $\tau_3$, $\tau_4$ is difference for each of the driving mode changes and each of the ingredients to be measured, the data of said concentration $C_E(t)$ of the ingredient gas put out from the gas concentration analyzer in real time have a form enlarged or compressed relatively to a time axis in each driving mode.

However, even though such a changing state of data is realistic, it has been quite disregarded in the prior methods. For example, both the measurement of the flow rate $Q_E(t)$ of the exhaust gas and the measurement of the concentration $C_E(t)$ of the ingredient gas have been carried out at equal time increments in a manner as shown by marks ○ in FIG. 5 (illustrating a case of the accelerating driving mode ACC). In short, as above described, both the measurement of the flow rate $Q_E(t)$ of the exhaust gas and the measurement of the concentration $C_E(t)$ of the ingredient gas have been carried out substantially without any delay relative to the points in time of changing over the driving mode, so that in each driving mode the sampling data of the concentration $C_E(t)$ of an ingredient gas corresponding to other driving modes are mixed and sampling data of the flow rate $Q_E(t)$ of the exhaust gas do not correspond to the sampling data of the concentration $C_E(t)$ at a ratio of 1:1 in phase, and number. Accordingly, even in a case of an average value method, in which an average quantity M of an ingredient gas is determined for each driving mode, a disadvantage has occurred in that an error of 20 to 30% is produced. In addition, in a case of an instantaneous operational method, in which a quantity $M(t)$ of an exhaust ingredient gas is measured and determined following successive time increments, the error in $M(t)$ is too large to be accepted.

However, recently required improvements in the performance of motor vehicles in view of governmental regulations of exhaust gas emissions, fuel-use efficiency and the like have been increasingly tightened up. In this sense, it has been eagerly desired to turn the instantaneous operational method, which is capable of investigating exhaust gas emission in greater detail to practical use (by improving its accuracy and simplifying its implementation).

OBJECT AND SUMMARY OF THE INVENTION

The present invention was achieved in view of the above. It is an object of the present invention to provide a novel method for a modal mass analysis of an exhaust from a motor vehicle capable of measuring a quantity of an ingredient gas to be measured in an exhaust gas with high accuracy by a comparatively simple operational method, not only in using an average value method, in which a quantity M of an average ingredient gas is determined for each driving mode, but also in performing an instantaneous operational method, in which a quantity M(t) of an exhausted ingredient gas is measured and determined in successive short time increments.

In accordance with the invention and in order to achieve the above described object, a modal mass analysis of an exhaust gas from a motor vehicle is performed by adopting such measures that in order to make the flow rate $Q_E(t)$ of the exhaust gas used in the above described operational equation (2) correspond to the concentration $C_E(t)$ of the ingredient gas to be measured used in the above described operation equation (2) at a ratio of 1:1 in each driving mode, sampling data relative to the flow rate $Q_E(t)$ are obtained by beginning measurements thereof substantially without any delay relative to a point of change-over time of each driving mode which sampling data $C_{ES}(t)$ relative to the concentration $C_E(t)$ of the ingredient to be measured is obtained with a time delay relative to the points of change-over time of each driving mode of an appointed time, depending on the ingredient gas and the changes in driving mode, and the concentration $C_{E1}(t)$ of the ingredient to be measured corresponding to said sampling data of the flow rate $Q_E(t)$ of the exhaust gas in the same phase from the sampling data $C_{ES}(t)$ of the concentration of the ingredient gas is determined by an interpolation method, and then the determined value of concentration is corrected by the data-compression method or the data-expansion method based on the following operation equation (3), to obtain the concentration $C_E(t)$ of the ingredient to be measured:

$$C_E(t) = C_{E1}(t) \times N_C/N_Q \quad (3)$$

wherein $N_C$, $N_Q$ are respective numbers of samplings of $C_E(t)$, $Q_E(t)$ taken in each mode at equal time increments in each driving mode, respectively, which numbers can be preliminarily determined in each driving mode. It is noted that $N_C/N_Q$ represents ratio of the time periods during which the concentration of the exhaust ingredient gas to be measured and the flow rate correspond to a particular driving mode. See, for example, FIG. 2.

Thus, according to a method of this invention, as will be further understood from the below description of preferred embodiments of the invention, since the flow rate $Q_E(t)$ of the exhaust gas used in said operation equation (2) is adapted to correspond to the concentration $C_E(t)$ of the ingredient gas to be measured used in the operation equation (2), the operation equation (2) can be used to determine an ever-changing quantity of the exhausted ingredient gas at a ratio of 1:1 in phase relation and number to the flow rate by setting appropriate delay times for the beginning and ending of the sampling of the data of the concentration of the ingredient gas for each driving mode, which is actually measured in an appointed sampling time, and subjecting the measured sampling data $C_{ES}(t)$ to a relatively simple operational correction by use of the interpolation method and the data-compression method or the data-expansion method. In this way, the quantity M(t) of the exhausted ingredient gas can be determined on a substantially continuous basis with remarkably high accuracy by said equation (2). Also, the average quantity M of the exhausted ingredient gas exhausted in each driving mode can be determined with remarkably high accuracy on the basis of the operational result of said quantity M(t). According to test results to date, it has been found that an error of measurement by the conventional method of 20 to 30% can be reduced to 5% by performing a modal mass analysis according to the invention.

Thus, in accordance with the method of the invention, not only an average value of the quantity of the ingredient gas to be measured in the exhaust gas from a motor vehicle in each driving mode, but also an ever-changing quantity of the ingredient to be measured in the exhaust gas from a motor vehicle can be measured with high accuracy, so that various kinds of performance of a motor vehicle in transient driving thereof can be investigated in detail.

In addition, since the operational correction of said concentration $C_E(t)$ of the ingredient gas to be measured in the method according to the invention can be performed by relatively simple steps, as above described, a calculating means such as a computer of relatively small capacity is sufficient for the realization of said operational correction, and thus the cost of the system for performing the modal mass analysis of exhaust gas from a motor vehicle is not substantially increased over that required to perform the prior method.

Furthermore, the method of the invention can be applied to all modal mass analyses such as the dilute stream method, the $CO_2$-tracing method and the dilution air quantity method.

BRIEF DESCRIPTION OF THE DRAWINGS

The preferred embodiments of a method of modal mass analysis of an exhaust gas from a motor vehicle according to the invention are shown in FIGS. 1 to 3, in which.

In addition, the technical background of the invention and the problems of the prior art are illustrated in FIGS. 4 and 5, in which.

DETAILED DESCRIPTION OF THE PREFERRED EMBODIMENTS

Figure 1:
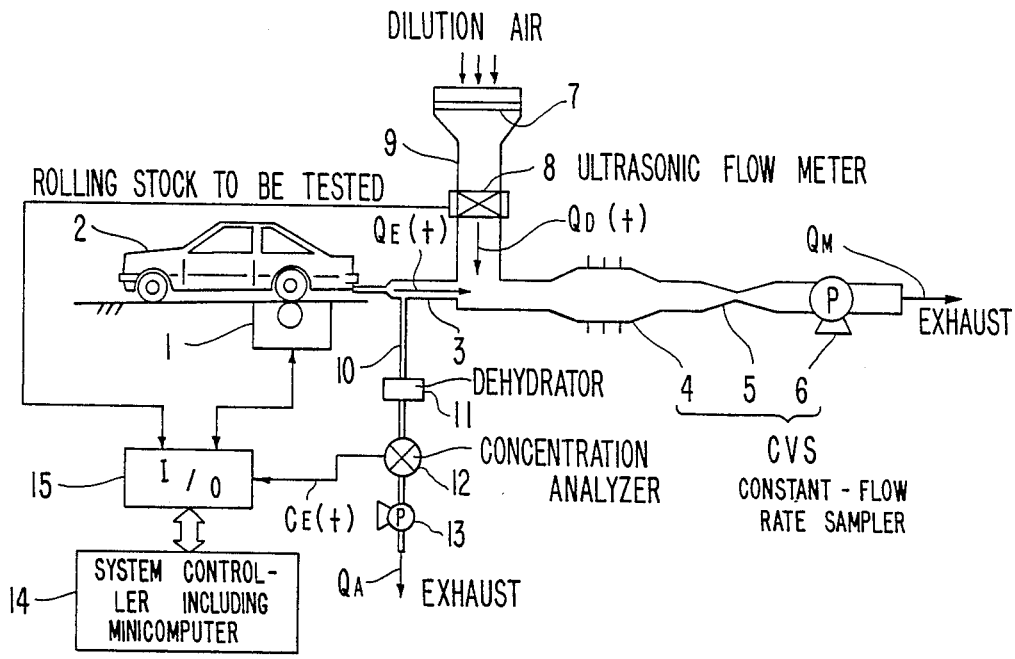
FIG. 1 is a schematic illustration of a modal mass analysis system, using a dilution-air quantity method to which a method of the invention is applied.
Figure 3:
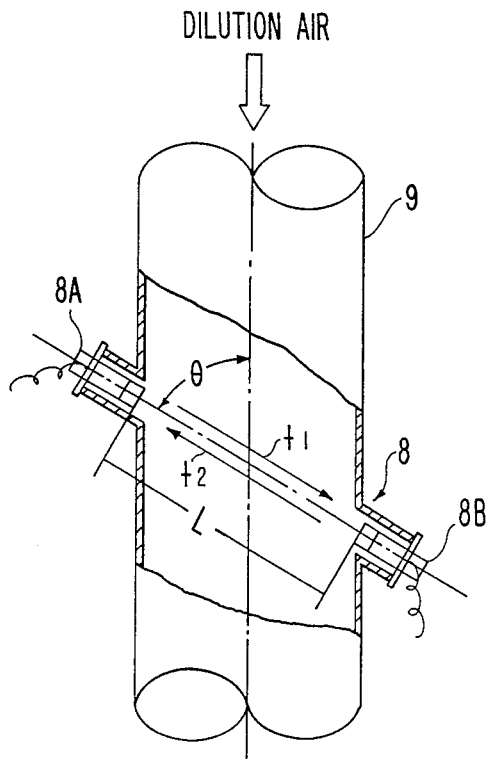
FIG. 3 is a diagram showing the principle of an ultrasonic flow meter.
Figure 2:
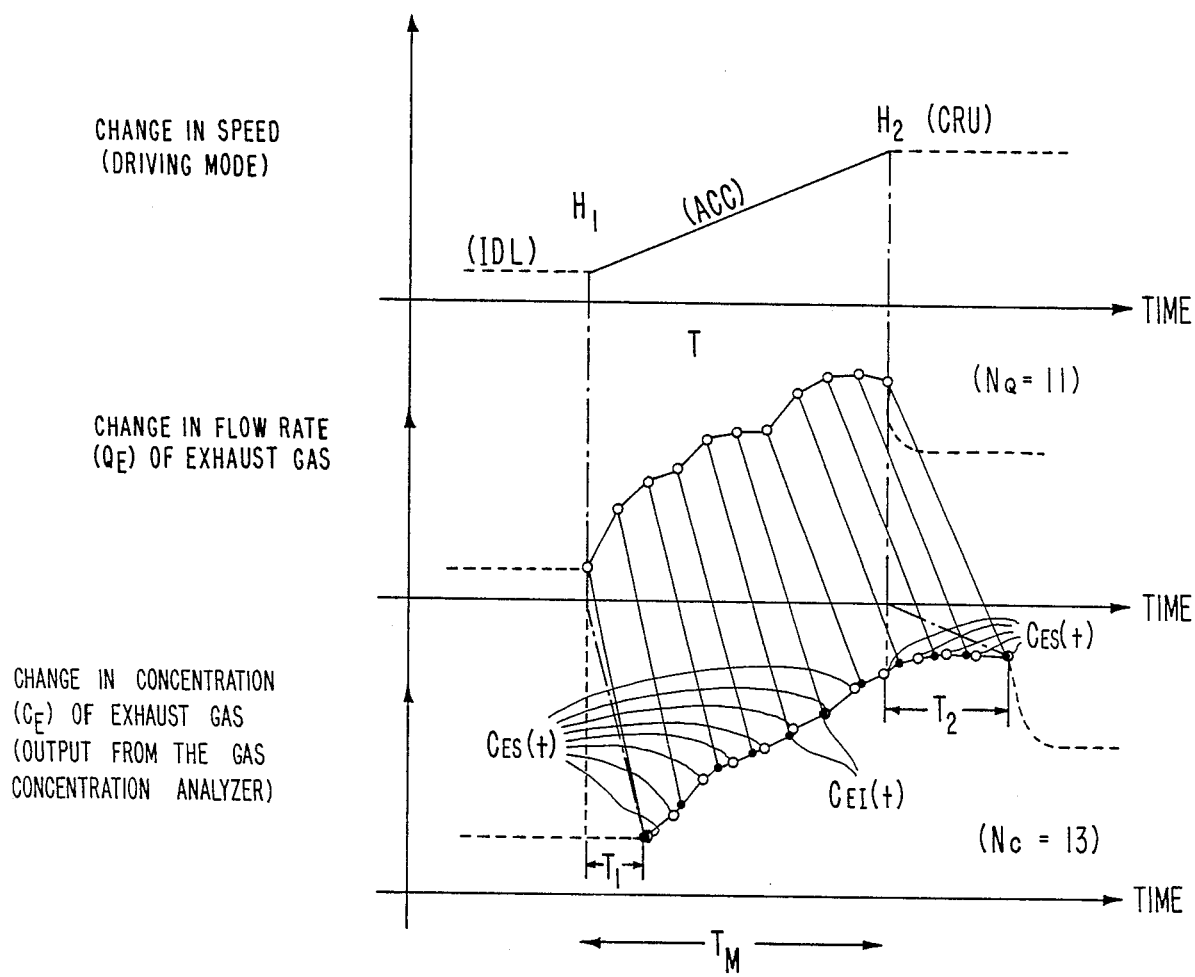
FIG. 2 is a schematic timing chart for explaining the fundamental principle of the method of the invention.

The preferred embodiments of the present invention will be below described with reference to the drawings (FIGS. 1 to 3).

FIG. 1 shows an outline of a construction of a modal mass analysis system based on the dilution air quantity method as one example of a modal mass analysis system for analyzing exhaust gas from a motor vehicle, for use in performing the method according to the invention.

Reference numeral 1 designates a chassis dynamometer as a motor vehicle-driving simulator adapted to simulate a condition that a motor vehicle is driven on an actual road while the vehicle is standing still, by absorbing a force generated from the vehicle or rolling stock 2. Since this chassis dynamometer 1 has been disclosed in detail U.S. Pat. No. 4,327,578 and the like, the description of its concrete construction is omitted herein.

The motor vehicle 2 to be tested is driven in various driving modes, including an idling driving mode (IDL), an accelerating driving mode (ACC), a constant-speed (cruising) mode (CRU), and a decelerating driving mode (DEC), by the chassis dynamometer 1 in an appointed sequence.

Reference numeral 3 designates an exhaust gas-inlet passage for introducing an exhaust gas exhausted from the rolling stock 2 to be tested, a constant-flow rate sampler CVS comprising a heat exchanger 4, a constant-flow rate Venturi portion 5, a constant-flow rate suction blower 6 and the like being connected to the exhaust gas-inlet passage 3, and a dilution air-inlet passage 9 provided with a filter 7 and an ultrasonic flowmeter 8 being connected to a joint between the exhaust gas-inlet passage 3 and the constant-flow rate sampler CVS.

Gas samples are led from the exhaust gas inlet passage 3 by a sampling passage 10 for measurement of the concentration of each of various kinds of specified ingredient gases (CO, $CO_2$, $NO_x$, HC and the like), a dehydrator 11 for dehydrating the exhaust gas at a specified temperature (for example 5° C.), a concentration analyzer 12 for analyzing various kinds of specified ingredient gases (the ingredient or ingredients to be measured) and a constant-flow rate suction blower 13 are provided in passage 10 in this order from an upstream side thereof.

Reference numeral 14 designates a system controller (including a calculating means) formed of, for example, a minicomputer and the like having a comparatively small capacity and adapted to carry out an operation for the chassis dynamometer 1 and simultaneously, to carry out an operational treatment for determining the quantity of the ingredient gas in the exhaust gas for each driving mode on the basis of a result of measurement of flow rate by means of the ultrasonic flow meter 8 in the dilution air-inlet passage 9 and the result of a measurement of concentration by means of the gas concentration analyzer 12 (the details of which will be described below). In addition, reference numeral 15 designates input-output (I/O) interfaces provided between the system controller 14 and the chassis dynamometer 1, the ultrasonic flow meter 8 and the gas concentration analyzer 12. Although not shown in the drawings, the system controller 14 is of course also provided with a control panel, a display device, a recorder, a memory device and the like connected thereto.

A principle of the operational treatment practically carried out by the system controller 14 for determining the quantity (mass) of the ingredient to be measured in the exhaust gas, in short the principle of a modal mass analysis of an exhaust gas from a motor vehicle according to the invention, is now described.

As is shown in FIG. 1, provided that a constant flow rate of an exhaust gas drawn in the sampling passage 10 for measuring a constant concentration is $Q_A$, a quantity of dilution air measured by the ultrasonic flow meter 8 in the dilution air-inlet passage 9 being $Q_D(t)$, and a constant total sunction flow rate by the constant-flow rate sampler CVS being $Q_M$, a flow rate $Q_E(t)$ of an exhaust gas from the rolling stock 2 to be tested is determined by the following operational equation (1):

$$Q_E(t) = Q_A + Q_M - Q_D(t) \tag{1}$$

On the other hand, provided that the concentration of the exhaust gas ingredient gas to be measured, measured by the gas concentration analyzer 12, is $C_E(t)$, a quantity (mass) $M(t)$ of the ingredient gas is determined by the following operational equation (2):

$$M(t) = \rho \times C_E(t), \tag{2}$$

wherein $\rho$ is the density of the ingredient gas to be measured.

Figure 4:
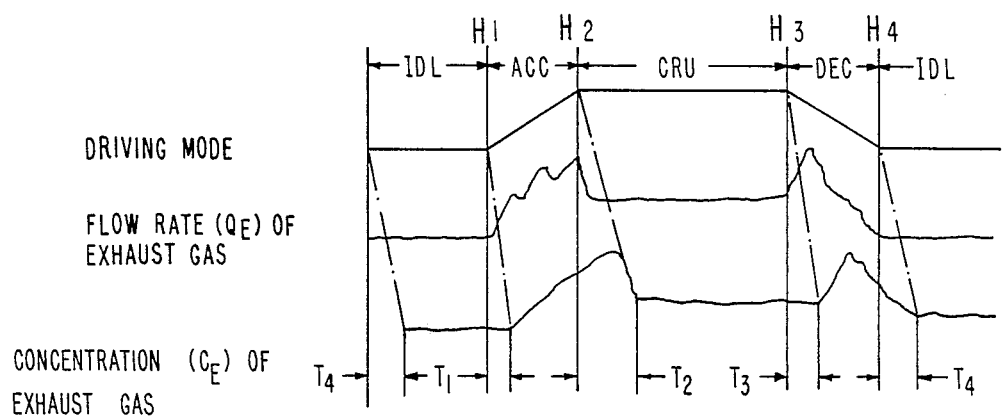
FIG. 4 is a general schematic timing chart of various kinds of data used in a modal mass analysis.
Figure 5:
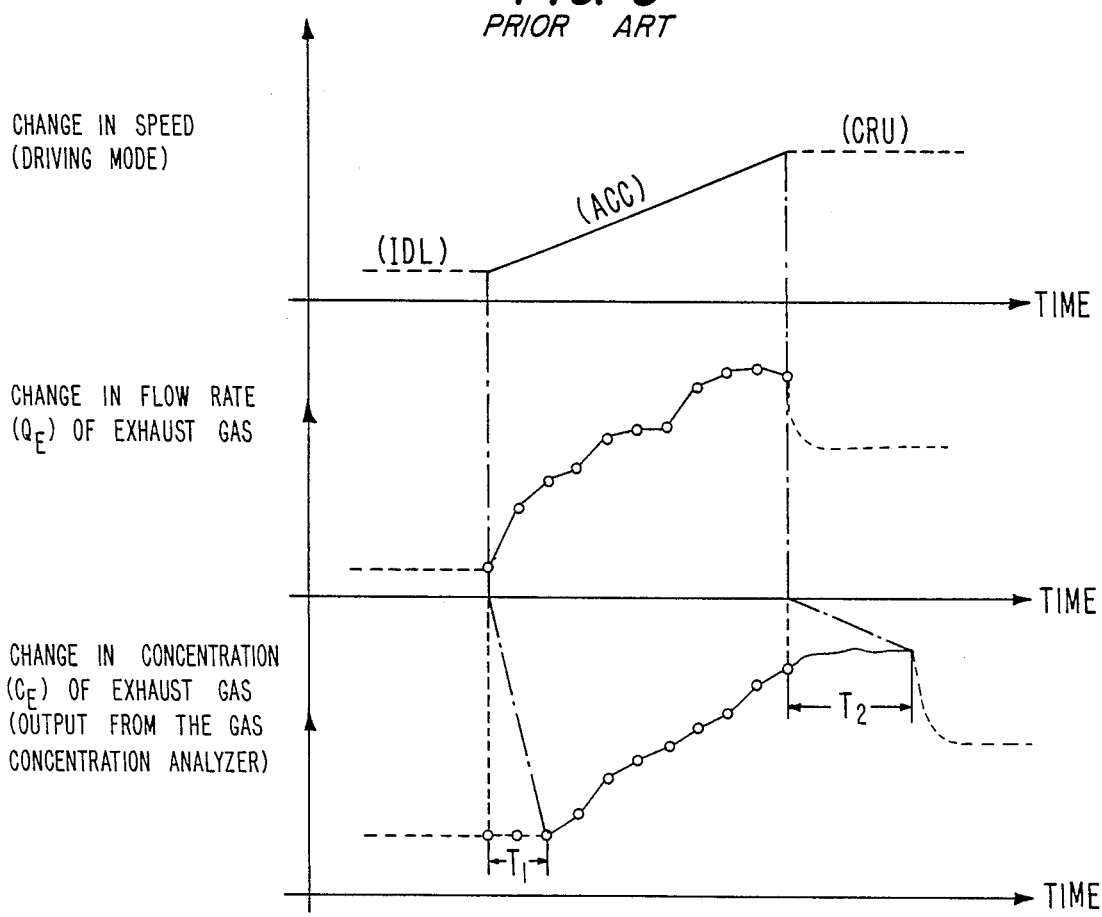
FIG. 5 is a schematic timing chart for explaining the conventional methods.

However, as is described above with reference to FIGS. 4 and 5, the flow rate $Q_E(t)$ of the exhaust gas is changed almost instantaneously at the changing-over times $H_1$, $H_2$, $H_3$, $H_4$ of driving modes, that is, without any delay, but the concentration $C_E(t)$ of the ingredient gas to be measured is changed only after certain delay times $\tau_1$, $\tau_2$, $\tau_3$, $\tau_4$ relative to each changing-over timing $H_1$, $H_2$, $H_3$, $H_4$ of driving modes, respectively. Moreover, the delay times $\tau_1$, $\tau_2$, $\tau_3$, $\tau_4$ are different for each driving mode change and each ingredient gas, so that there is a general tendency that the data of the concentration $C_E(t)$ of the ingredient gas put out from the gas concentration analyzer 12 in real time take a form relatively expanded or compressed relative to the time in each driving mode. Accordingly, in the method of the invention, in order to make the flow rate $Q_E(t)$ of the exhaust gas used in the operational equation (2) correspond to the concentration $C_E(t)$ of the ingredient gas used in said operational equation (2) in a ratio of 1:1 in each driving mode, the sampling of the dilution-air quantity $Q_D(t)$ measured by the ultrasonic flow meter 8 and the concentration $C_E(t)$ of the ingredient gas measured by the gas concentration analyzer 12 and the treatment of the sampling data are carried out as follows:

As is shown in FIG. 2 (illustrating measurements taken during an accelerating driving mode ACC), sampling data of dilution-air quantity $Q_T(t)$ is obtained by taking measurements at equal time increments over the entire appointed time of the particular driving mode substantially without any delay relative to a point of changing-over time of each driving mode for use in the operational equation (1). This is expressed as a sampling result (shown by marks ○) of the flow rate $Q_E(t)$ of the exhaust gas, in FIG. 2. Sampling data of the concentration of the ingredient gas to be measured $C_{ES}(t)$ is obtained by taking measurements at time increments of the same length as those of $Q_D(t)$ with predetermined delays for beginning and ending relative to the points of changing-over time of the driving modes depending on the ingredient to be measured and the change in driving modes (the appointed beginning and ending time delays being an experimentally determined $\tau_1$ and $\tau_2$ respectively after commencement and completion of the accelerating driving mode in the illustrated embodiment).

Simultaneously, the concentrations $C_{E1}(t)$ of the ingredient to be measured (shown by marks ●) corresponding to the sampling data of the flow rate $Q_E(t)$ of the exhaust gas in the same phase on the basis of the sampling data $C_{ES}(t)$ (shown by marks ○) of the concentration of the ingredient gas to be determined by the interpolation method is determined. Simultaneously with the acquisition of the sampling data $C_{ES}(t)$ and following the application of the interpolation method, to determine the values covered by $C_{E1}(t)$, the concentration values $C_{E1}(t)$ are subjected to a concentration correction procedure by the data-compression method or the data-expansion method based on the following operational equation (3) so as to compensate for the increase or decrease in the magnitude of the sampling data $C_{ES}(t)$ and thus values $C_{E1}(t)$ caused by the difference in the delay times $\tau_1$ and $\tau_2$, and thereby to obtain the concentration $C_E(t)$ of the ingredient to be measured used in said operational equation (2):

$$C_E(t) = C_{E1}(t) \times N_C/N_Q, \quad (3)$$

wherein $N_C$ and $N_Q$ are the numbers of samplings of $C_E(t)$ and $Q_E(t)$, respectively, which numbers can be preliminarily determined by experiment and/or calculation in order that the samplings appropriately correspond to the driving mode, that is, are taken within the time periods during which the samplings correspond to the driving mode (see FIG. 2), the ratio $N_C/N_Q$ being equal to the ratio of the time periods in which the concentration and flow rate samplings are taken. Thus, in equation (3), $N_C/N_Q$ may be expressed as follows:

$$N_C/N_Q = 1 + (\tau_{i+1} - \tau_i)/(H_{i+1} - H_i)$$

where $i = 1$, 2 or 3 and $H_{i+1} - H_i$ is equal to the time period $T_M$ of the driving mode and the time periods $\tau_1$, $\tau_2$, $\tau_3$, $\tau_4$ are determined by previous experiment.

However, even though the measurement of the concentration $C_E(t)$ of each ingredient to be measured is carried out for the exhaust gas after it has been dehydrated at a specified temperature of T° C. (for example 5° C.), the measurement of the dilution-air quantity $Q_D(t)$ for determining the flow rate $Q_E(t)$ of the exhaust gas is carried out without such dehydration, so that in this embodiment a value $Q_{ET}(t)$ obtained by subjecting the flow rate $Q_E(t)$ determined by said operational equation (1), to the humidity correction for the hydrating condition at the specified temperature of T° C., is used as the flow rate $Q_E(t)$ of the exhaust gas used in said operation equation (2).

More specifically, the flow rate $Q_{ET}(t)$ under the hydrated condition at the specified temperature of T° C. is determined by the following operational equation (4) in which the flow rate $Q_E(t)$ determined by the operational equation (1), the CO-concentration $a(t)$, the $H_2O$-concentration $d(t)$ and the CH (carbon-hydrogen) ratio $y$ of the fuel used at said specified temperature of T° C., are used:

$$\begin{aligned} Q_{ET}(t) &= Q_E(t)[1 + d(t) - X(t)] \\ X(t) &= \frac{y/2\,[a(t) + b(t) + 3c(t)] - 4c(t)}{a(t)/3.8b(t) + 1} \end{aligned} \quad (4)$$

In short, summarizing the above description, a modal mass analysis of an exhaust gas from a motor vehical according to the present invention uses the equation (2) $(M(t) = \rho \times C_E(t) \times Q_{ET}(t))$ as the fundamental operational equation and the equation (1), the equation (3) and the like as auxiliary operational equations.

The principle of the measurement of the dilution-air quantity $Q_D(t)$ by means of the ultrasonic flow meter 8 located in the filution-air inlet passage 9 will now be described with reference to FIG. 3.

The ultrasonic flow meter 8 is fundamentally used for measuring the flow rate and is composed of two ultrasonic transmitter/receiver sets 8A and 8B arranged opposite to each other at an angle of $\theta$ to the dilution-air inlet passage 8, whereby it is hardly influenced by a pressure loss.

Provided that a distance between the ultrasonic transmitter/receivers 8A and 8B is L, the propagation speed of an ultrasonic wave from the ultrasonic transmitter/receiver 8A to the ultrasonic transmitter/receiver 8B being $t_1$, the propagation speed of an ultrasonic wave from the ultrasonic transmitter/receiver 8B to the ultrasonic transmitter/receiver 8A being $t_2$, the angle between a central axis of the dilution-air inlet passage 9 and the ultrasonic wave propagation axis of the ultrasonic transmitter/receivers 8A and 8B being $\theta$, the average linear flow rate on a line between the ultrasonic transmitter/receiver sets 8A, 8B in the dilution-air inlet passage 9 being V, and the propagation speed of an ultrasonic wave in a stationary gas being $t_o$, then $t_1$ and $t_2$ are related to L, $t_o$, V and $\theta$ as follows:

$$t_1 = L/(t_o + V\cos\theta)$$

and $$t_2 = L/(t_o - V\cos\theta).$$

Accordingly, solving the above equations for V:

$$V = \frac{L}{2\cos\theta}\left(\frac{1}{t_1} - \frac{1}{t_2}\right)$$

An average flow rate $V_s$ per unit sectional area in the dilution-air inlet passage 9 is expressed by the following well known Plandtl's equation:

$$V_s = V \times \frac{1}{1 + 0.01\sqrt{6.25 + 431 Re^{-0.237}}}$$

where Re is the Reynolds number.

Accordingly, provided that the cross-sectional area of the dilution-air inlet passage 9 is S, the temperature of a liquid under standard conditions being $T_o$ (for example 25° C.), the pressure of the liquid under standard conditions being $P_o$ (for example 1 atmosphere), the temperature of the liquid under the operating conditions being T, and the pressure of the liquid under the operating conditions being P, said dilution-air quantity $Q_D(t)$ at the standard condition can be determined by the following operational equation:

$$Q_D(t) = V_s \times S \times \frac{T_o \times P}{T \times P_o}$$

As is apparent from the above detailed description, according to a method of performing a modal mass analysis of an exhaust gas from a motor vehicle of the invention, the flow rate $Q_E(t)$ of the exhaust gas used in the operational equation (2) for determining the momentary quantity of the ingredient gas to be measured is adapted to correspond to the concentration $C_E(t)$ of the ingredient gas used in the operational equation (2) at a ratio of 1:1 in phase relation and number (magnitude based on the relative times over which the measurements are taken) by setting a delay time for the beginning of the sampling of the data of the ingredient to be measured and subjecting the measured sampling data $C_{ES}(t)$ to a relatively simple operational correction to which the interpolation method and the data-compression method or the data-expansion method are applied by the operational equation (3), so that the quantity M(t) of the exhausted ingredient to be measured can be determined on a substantially continuous basis with very high accuracy by the operational equation (2), whereby also the average quantity M of the exhausted ingredient gas to be measured in each driving mode can be determined with remarkably high accuracy on the basis of the operation result. Thus, various kinds of performance of a motor vehicle during transient driving can be investigated in remarkably greater detail and with higher accuracy in comparison with the conventional $C_E(t)$ of the ingredient gas to be measured according to the method of the invention is based on a relatively simple method, so that various superior effects have been exhibited in that a calculating means of a relatively small capacity is sufficient for carrying out the method and the construction of a modal mass analysis system of an exhaust gas from a motor vehicle is remarkably advantageous in cost.

What is claimed is:

1. A method of measuring the quantity of an ingredient gas in the exhaust gas from a motor vehicle during the time period of each of a sequence of driving modes, the time period of each driving mode having a starting time and an ending time, the ending time of the time period of each driving mode being the starting time of the time period of the next driving mode in the sequence, the method comprising for each driving mode in the sequence, the steps of:

measuring and storing data representative of the flow rate $Q_E(t)$ of the exhaust gas at a succession of times, $N_Q$ in number, including the starting time and the ending time, during the time period of the driving mode;

measuring and storing data $C_{ES}(t)$ representative of the concentration of the ingredient gas in the exhaust gas at successive times, $N_C$ in number, beginning at a time delayed relative to the starting time by a first predetermined amount of time dependent upon the change in driving mode at the starting time and the ingredient gas and ending at a time delayed relative to the ending time by a second predetermined amount of time dependent upon the change in driving mode at the ending time and the ingredient, such that the first measurement of concentration corresponds to the flow rate $Q_E(t)$ at the starting time and the $N_C$th measurement of concentration corresponds to the flow rate $Q_E(t)$ at the ending time;

performing an interpolation method on the stored data $C_{ES}(t)$ to obtain, and then store, values $C_{E1}(t)$ representative of the concentration of the ingredient gas in the exhaust gas corresponding to, and at times in the same phase as, the stored data representative of the flow rate $Q_E(t)$, and then correcting the values representative of the concentration $C_{E1}(t)$ to obtain corrected values $C_E(t)$ representative on a one-to-one basis in phase and magnitude to the flow rate $Q_E(t)$ by one of a data-compression method and a data-expansion method based on the operational equation $C_E(t) = C_{E1}(t) \times N_C/N_Q$; and determining the quantity $M(t)$ of the ingredient gas in the exhaust gas for each of the succession of times during the time period based on the operational equation $M(t) = \rho \times C_E(t) \times Q_E(t)$, where $\rho$ is the density of the ingredient.

2. A method of measuring the quantity of an ingredient gas in the exhaust gas from a motor vehicle during the time period of each of a sequence of driving modes, the time period of each driving mode, being of length $T_M$, having a starting time and an ending time, the ending time of the time period of each driving mode being the starting time of the time period of the next driving mode in the sequence, the method comprising for each driving mode in the sequence, the steps of:

measuring and storing data representative of the flow rate $Q_E(t)$ of the exhaust gas at a succession of times during the time period of the driving mode;

measuring and storing data $C_{ES}(t)$ representative of the concentration of the ingredient gas in the exhaust gas at successive times only during a period of time beginning at a time delayed relative to the starting time by a first predetermined amount of time $\tau_1$ dependent upon the change in driving mode at the starting time and the ingredient and ending at a time delayed relative to the ending time by a second predetermined amount of time $\tau_2$ dependent upon the change in driving mode at the ending time and the ingredient gas;

performing an interpolation method on the stored data $C_{ES}(t)$ to obtain, and then store, values $C_{E1}(t)$ representative of the concentration of the ingredient in the exhaust gas corresponding to, and at times in the same phase as, the stored data representative of the flow rate $Q_E(t)$, and then correcting the values representative of the concentration $C_{E1}(t)$ to obtain corrected values $C_E(t)$ representative on a one-to-one basis in phase and magnitude to the flow rate $Q_E(t)$ by one of a data-compression method and a data-expansion method based on the operational equation $C_E(t) = C_{E1}(t) \times (1 + (\tau_2 - \tau_1)/T_M)$; and determining the quantity $M(t)$ of the ingredient gas in the exhaust gas for each of the succession of times during the time period of the driving mode based on the operational equation $M(t) = \rho \times C_E(t) \times Q_E(t)$, where $\rho$ is the density of the ingredient gas.

* * * * *